US008500631B2

United States Patent
Stokes et al.

(10) Patent No.: US 8,500,631 B2
(45) Date of Patent: Aug. 6, 2013

(54) METHODS AND DEVICES FOR PERCUTANEOUS ILLUMINATION

(75) Inventors: Michael Stokes, Cincinnati, OH (US);
Mark S. Ortiz, Milford, OH (US);
David N. Plescia, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1336 days.

(21) Appl. No.: 11/277,549

(22) Filed: Mar. 27, 2006

(65) Prior Publication Data

US 2007/0225573 A1    Sep. 27, 2007

(51) Int. Cl.
*A61B 1/06* (2006.01)

(52) U.S. Cl.
USPC .......................................... 600/178; 600/249

(58) Field of Classification Search
USPC .... 600/178, 179, 249, 146, 180–182; 607/92; 362/120, 198, 574
See application file for complete search history.

(56) References Cited

U.S. PATENT DOCUMENTS

| | | | | |
|---|---|---|---|---|
| 902,513 A | * | 10/1908 | Wappler | 600/179 |
| 1,453,297 A | * | 5/1923 | Wappler | 600/178 |
| 1,509,041 A | * | 9/1924 | Hyams | 433/29 |
| 3,699,950 A | * | 10/1972 | Humphrey et al. | 600/249 |
| 4,534,339 A | * | 8/1985 | Collins et al. | 600/136 |
| 4,838,245 A | * | 6/1989 | Storz | 600/139 |
| 4,927,021 A | * | 5/1990 | Taylor | 206/373 |
| 4,967,323 A | * | 10/1990 | Johnson et al. | 362/103 |
| 5,051,876 A | * | 9/1991 | Norman | 362/120 |
| 5,122,122 A | * | 6/1992 | Allgood | 604/174 |
| D329,823 S | * | 9/1992 | Francisco | D10/104 |
| 5,147,316 A | | 9/1992 | Castillenti | |
| 5,334,150 A | * | 8/1994 | Kaali | 604/164.08 |
| 5,392,917 A | * | 2/1995 | Alpern et al. | 206/570 |
| 5,545,179 A | * | 8/1996 | Williamson, IV | 606/213 |
| 5,797,929 A | * | 8/1998 | Andreas et al. | 606/148 |
| 5,928,137 A | * | 7/1999 | Green | 600/160 |
| 5,964,004 A | | 10/1999 | Bean | |
| 5,976,075 A | * | 11/1999 | Beane et al. | 600/146 |
| 6,000,809 A | * | 12/1999 | Belo | 362/118 |
| 6,033,411 A | * | 3/2000 | Preissman | 606/99 |
| 6,352,503 B1 | * | 3/2002 | Matsui et al. | 600/104 |
| 6,432,046 B1 | * | 8/2002 | Yarush et al. | 600/179 |

(Continued)

FOREIGN PATENT DOCUMENTS

| | | |
|---|---|---|
| JP | 04-226620 A | 8/1992 |
| JP | 07-136176 A | 5/1995 |

(Continued)

OTHER PUBLICATIONS

Chinese Office Action for Application No. 200710091545.8 issued Dec. 3, 2012. (5 pages).

(Continued)

*Primary Examiner* — Jan Christopher Merene

(57) ABSTRACT

Methods and devices for illuminating a body cavity or an internal region of a body are disclosed. In one aspect, a percutaneous illumination device for illuminating a body cavity includes an elongate member with an illumination source, and two support members disposed on the elongate member that are adapted to be positioned on opposite sides of a tissue surface for stabilizing the device. Variations on such an illumination device, kits that include such devices, and methods of utilizing such devices are all described within the present application.

21 Claims, 5 Drawing Sheets

U.S. PATENT DOCUMENTS

| | | | |
|---|---|---|---|
| 7,478,917 B2 * | 1/2009 | Yu | 362/188 |
| 7,582,071 B2 * | 9/2009 | Wenchell | 604/167.06 |
| 2002/0052597 A1 * | 5/2002 | Duhaylongsod et al. | 606/15 |
| 2002/0096183 A1 | 7/2002 | Stevens et al. | |
| 2002/0131263 A1 * | 9/2002 | Naghi et al. | 362/98 |
| 2002/0156344 A1 * | 10/2002 | Pasricha et al. | 600/113 |
| 2003/0135091 A1 | 7/2003 | Nakazawa et al. | |
| 2003/0208187 A1 | 11/2003 | Layer | |
| 2004/0111061 A1 * | 6/2004 | Curran | 604/174 |
| 2005/0197536 A1 * | 9/2005 | Banik et al. | 600/179 |
| 2005/0203561 A1 | 9/2005 | Palmer et al. | |
| 2006/0217666 A1 * | 9/2006 | Wenchell | 604/167.03 |
| 2006/0235269 A1 * | 10/2006 | Waxman | 600/104 |

FOREIGN PATENT DOCUMENTS

| | | | |
|---|---|---|---|
| JP | 08-098799 A | 4/1996 | |
| JP | 10-108824 A | 4/1998 | |
| JP | 11-503646 A | 3/1999 | |
| JP | 2000-245689 A | 9/2000 | |
| JP | 2001-145634 A | 5/2001 | |
| JP | 2002-224129 A | 8/2002 | |
| JP | 2002-282202 A | 10/2002 | |
| JP | 2003-204920 A | 7/2003 | |
| JP | 2005-052442 A | 3/2005 | |

OTHER PUBLICATIONS

Japanese Office Action for Application No. 2007-079638 issued Mar. 27, 2012. (3 pages).

Japanese Office Action for Application No. 2007-079638 issued Feb. 19, 2013. (4 pages).

* cited by examiner

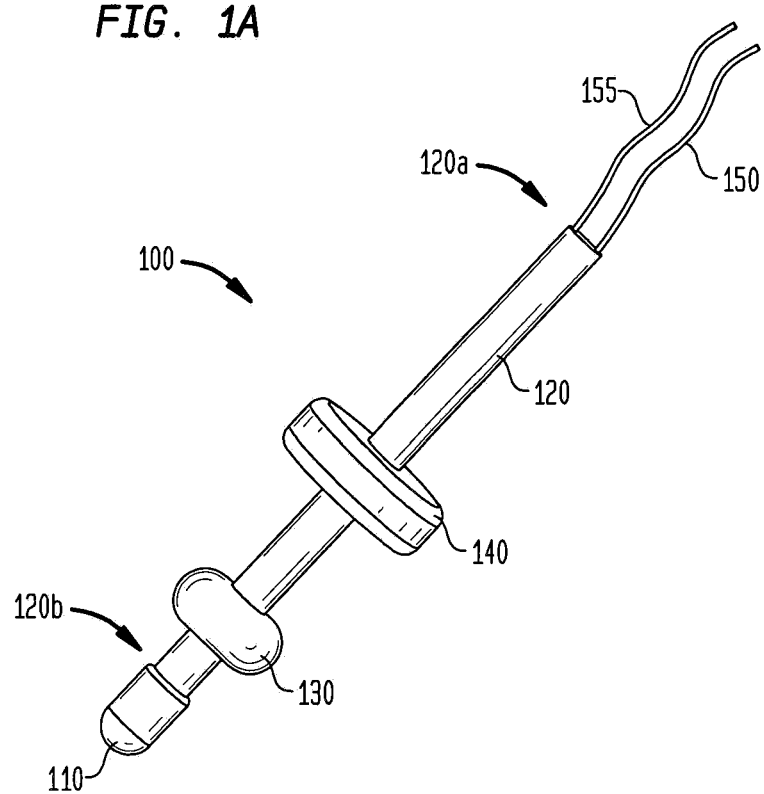

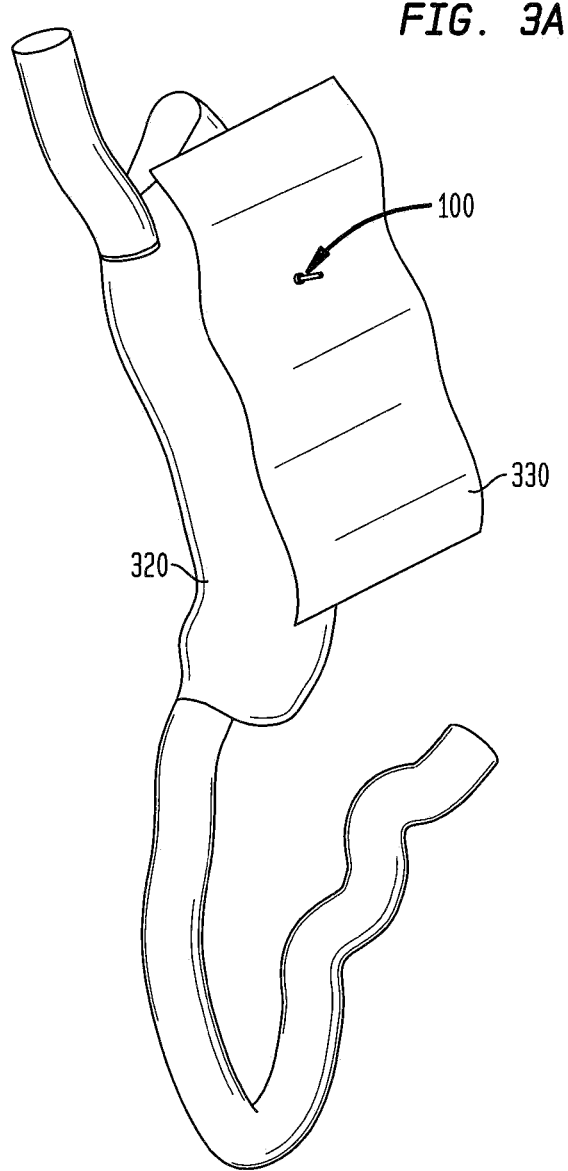

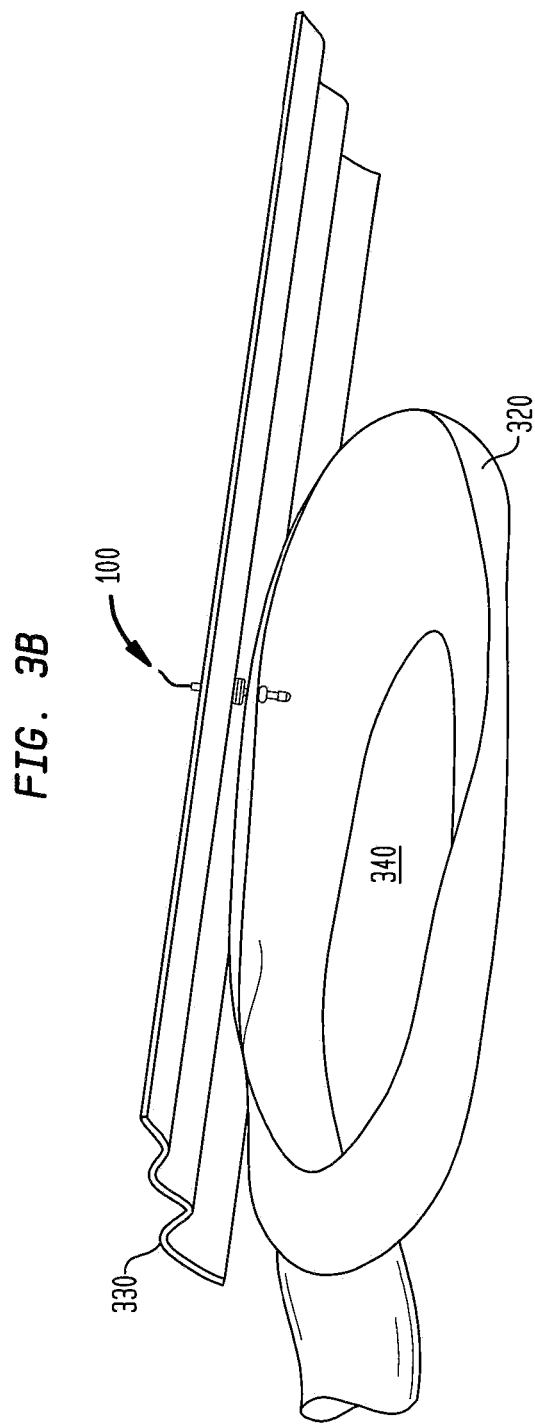

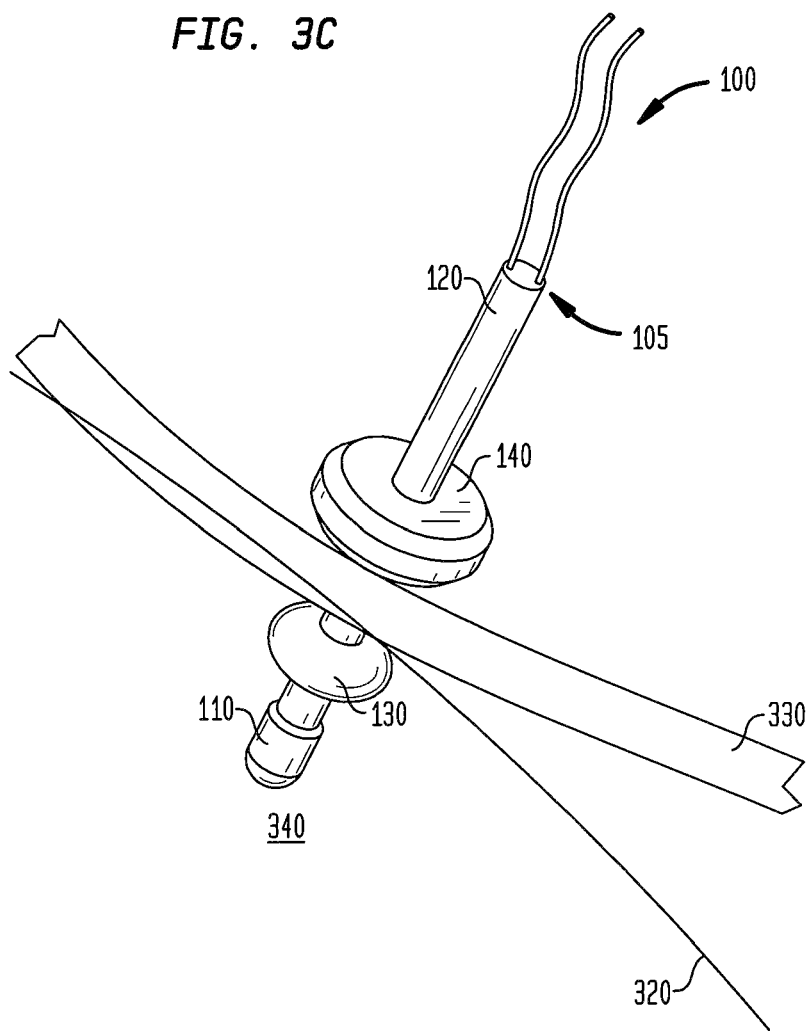

METHODS AND DEVICES FOR PERCUTANEOUS ILLUMINATION

FIELD OF THE INVENTION

The present invention relates broadly to devices and methods for illuminating an internal region of a patient.

BACKGROUND OF THE INVENTION

Endoscopic and laparoscopic surgical instruments are often preferred over traditional open surgical devices since the use of natural orifices (endoscopic) or smaller incisions (laparoscopic) tends to reduce the post-operative recovery time and complications. Consequently, a range of endoscopic and laparoscopic surgical instruments that are suitable for precise placement of a distal end effector at a desired surgical site have been developed. These distal end effectors engage the tissue in a number of ways to achieve a diagnostic or therapeutic effect (e.g., grasper, cutter, staplers, clip applier, access device, drug/gene therapy delivery device, and energy device using ultrasound, RF, laser, etc.).

Proper operation of endoscopic and laparoscopic surgical instruments is facilitated by adequate illumination of a body cavity into which such instruments are inserted. Current endoscopes and laparoscopes are not always capable of providing optimal lighting. For example, when an endoscope is inserted into a patient's stomach, the illumination provided by the scope can present shadows in the far-field that can be aggravated by the rough and wavy features of the gastric surface. Such shadowed areas can be difficult to eliminate due to the confining configuration that a scope operates within. Furthermore, endoscopes and laparoscopes do not always provide sufficient illumination, and the size of such scopes may limit the ability to provide additional lighting.

Accordingly, a need exists for devices and methods for improving illumination during endoscopic and laparoscopic procedures. Such devices and methods can also potentially provide improved illumination for other types of surgical procedures.

SUMMARY OF THE INVENTION

The present invention generally provides percutaneous illumination devices and methods for illuminating a body cavity. In one embodiment, an illumination device is provided and can direct light from one or more illumination sources, such as a light emitting diode disposed on the terminal end of the elongate member, configured to illuminate an area around an elongate member. The illumination device can include one or more optical fibers coupled to the elongate member for delivering light from the illumination source to an area surrounding the elongate member. An energy source, optionally coupled to the elongate member, can be in electrical communication with each illumination source. Two support members can also be disposed on the elongate member and adapted to be positioned on opposite sides of a tissue surface to stabilize the elongate member. The support members can be spaced apart by a distance that accommodates tissue being disposed therebetween. In certain exemplary embodiments, the support members can be in the form of flanges formed around the elongate member, or they can be in the form of an expandable structure that can have a dual configuration: one for insertion into tissue and one for engaging tissue. The elongate member can also include an adjustable joint, such as a ball and socket joint, which can be adapted to allow a distal portion of the elongate member to be positioned at an angle relative to a proximal portion of the elongate member. In other embodiments, the elongate member can include a penetrating tip configured to penetrate through tissue, and/or an attachment structure for receiving a suture.

Another embodiment is directed toward a kit for illuminating an internal region of a patient's body. The kit can include a set of illuminating devices. Each device can include an elongate body adapted to be inserted through tissue, and at least one illumination source for illuminating a region around the device. At least one of the devices can include an adjustable joint for positioning a distal portion of the device at an angle relative to a proximal portion of the device. A set of support devices can also be included, with each support device being adapted to stabilize an illuminating device at a desired angular orientation relative to the tissue. The kit can also include a set of energy sources configured to be electrically coupled to the illumination source of at least one of the illuminating devices.

In another exemplary embodiment, a method of illuminating a body cavity is provided and includes inserting an illumination device into tissue such that one end of the device is positioned within a body cavity (e.g., a stomach). Another end of the device can be positioned on an opposite side of a tissue layer relative to the end positioned within the body cavity. Insertion can be performed, for example, by delivering the illumination device using an endoscopic or laparoscopic technique, followed by penetrating the device through a body cavity wall. Alternatively, the insertion can be performed by penetrating the illumination device through dermal tissue before penetrating the body cavity wall. Insertion of the illumination device can also include coupling the device to a needle, and inserting the needle through tissue to thereby insert the illumination device. One or more tissue-engaging members, such as flanges, can be positioned adjacent to the tissue to anchor the device relative to the tissue. The device can then be activated to illuminate the body cavity. In addition, the direction of illumination of the device can be adjusted. In an exemplary embodiment, a plurality of illumination devices can be inserted to provide a desired amount of illumination in the body cavity.

BRIEF DESCRIPTION OF THE DRAWINGS

The invention will be more fully understood from the following detailed description taken in conjunction with the accompanying drawings, in which:

FIG. 1A is a perspective view of one embodiment of a percutaneous illumination device;

FIG. 3A is a perspective view of a stomach and a cutaway view of an abdominal wall, showing the percutaneous illumination device of FIG. 1A penetrating both tissue walls;

FIG. 3B is a magnified, cutaway perspective view of the stomach lining and abdominal wall of FIG. 3A showing the percutaneous illumination device penetrating both tissue walls;

FIG. 3C is a magnified perspective view of the percutaneous illumination device shown in FIGS. 3A and 3B.

DETAILED DESCRIPTION OF THE INVENTION

Figure 1B:
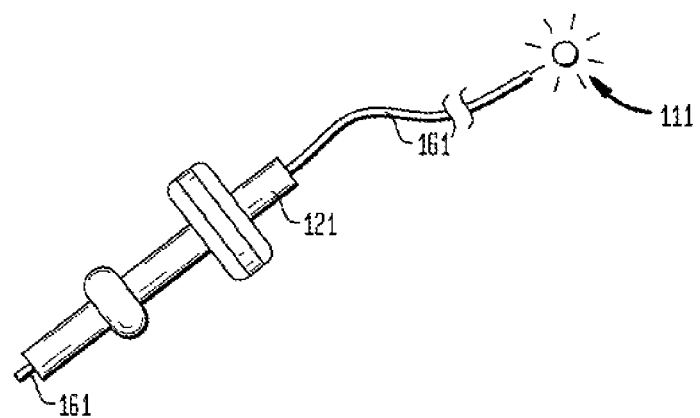
FIG. 1B is a side view of an embodiment of a percutaneous illumination device utilizing a remote illumination source.

Certain exemplary embodiments will now be described to provide an overall understanding of the principles, structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with features of other embodiments. Such modifications and variations are intended to be included within the scope of the present invention.

The present invention provides methods and devices for illuminating a body cavity, preferably during laparoscopic and endoscopic procedures. In particular, one or more illumination devices can be percutaneously inserted through tissue to direct light from one or more illumination sources within a body cavity. The illumination source(s) are effective to illuminate the body cavity, thereby allowing other procedures to be performed within the body cavity. While any body cavity can be illuminated, in an exemplary embodiment the body cavity is the stomach. The illumination device(s) can be positioned through the abdominal and stomach walls to illuminate the stomach, thereby allowing other procedures, such as gastric bypass and restriction procedures, to be laparoscopically or endoscopically performed within the stomach under illumination.

FIG. 1A illustrates one exemplary embodiment of a percutaneous illumination device 100 that can be used to illuminate a body cavity. The device 100 generally includes an elongate member 120 configured to direct light from an illumination source 110 to a region surrounding the elongate member 120. One or more support members can be coupled to the elongate member 120 to stabilize the illumination device 100. The embodiment depicted in FIG. 1A illustrates two support members 130, 140 adapted to be positioned on opposite sides of a tissue surface to stabilize the device 100 relative to the tissue. The device can also include other features such as leads 150, 155 for delivering energy to the illumination source 110, one or more suture-retaining members for mating a suture to the devices and other features to facilitate use of the device.

Figure 2:
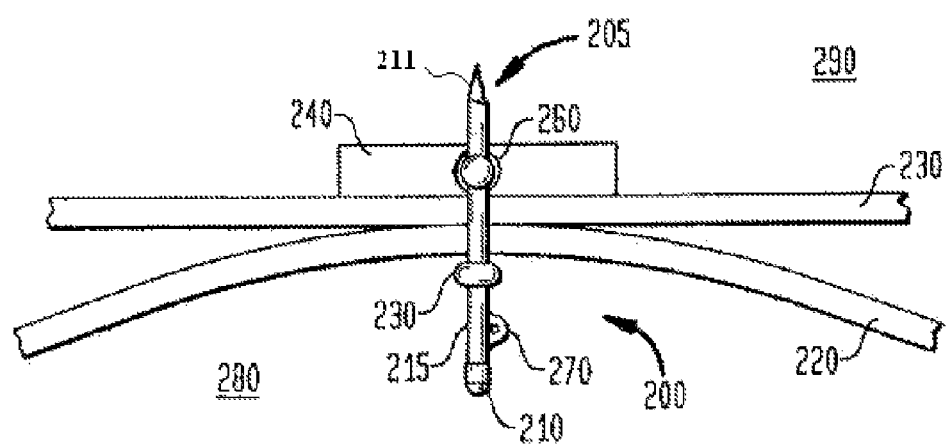
FIG. 2 is a side view of another embodiment of a percutaneous illumination device that includes an adjustable joint for orienting the illumination device.

The elongate member 120 of the device 100 can have a variety of configurations, and it can be a rigid or flexible, substantially solid or hollow body. In an exemplary embodiment, the elongate member 120 is hollow to allow the leads 150, 155 to extend therethrough. The elongate member 120 can also includes a tissue-penetrating tip formed on one end thereof for facilitating insertion through tissue. Alternatively, the elongate member 120 can include a suture-receiving element formed thereof to allow the elongate member 120 to be coupled to a suture and pulled through tissue using the a needle and the suture. FIG. 2 illustrates one exemplary embodiment of a percutaneous illumination device 200 having an elongate member 215 with a suture-receiving element 270 formed thereon. The suture-receiving element can be in the form of a bore or hole formed at any location along the elongate member. As shown in FIG. 2, the suture-receiving element 270 is in the form of an eyelet that is coupled to the elongate member 200 adjacent to an illumination source 210 on the terminal end of the elongate member 215.

Turning back to FIG. 1A, the elongate member 120 also preferably has a diameter that is sized to allow the device to be introduced percutaneously, and has a length that is configured to allow the illumination source 110 on the distal end 120b of the elongate member 120 to be positioned within a body cavity while the proximal end 120a remains outside of the body cavity. While the particular dimensions can vary depending on the intended use, in one exemplary embodiment the elongate member has a diameter in the range of about 1 millimeters to about 5 millimeters, and a length in the range of about 25 millimeters to about 300 millimeters.

The illumination source associated with the device can also have a variety of configurations, and it can be coupled to, disposed within, or formed on the elongate member 120 at various locations. In the embodiment shown in FIG. 1A, the illumination source 110 is fixedly coupled to the distal-most end 120b of the elongate member 110, and it is in the form of a light emitting diode 110. Other potential illumination sources can also be utilized such as a xenon bulb. In such an instance, the bulb 111 can remotely create light that is piped via a fiber optic 161 to the elongate member 121 and suitably directed, as shown in FIG. 1B. Though the illumination source 110 for the device 100 shown in FIG. 1A is positioned at a terminal end of the elongate member 120, the illumination source can be coupled to the elongate member at a variety of other locations. For example, the illumination source can be located at some position between the proximal and distal ends 120a, 120b of the elongate member 120 to allow a tip of the elongate member to be shaped and/or constructed to penetrate tissue. Alternatively, one end of the elongate member 120 can be configured with the penetrating tip 211 in FIG. 2, while the opposite end has the illumination source attached thereto. In use, energy can be provided to the illumination source using a variety of techniques. As depicted in FIG. 1A, first and second leads 150, 155 extend through the elongate member 120 and serve as an electrical connection between the illumination source 110 and an external power source. Alternatively, a small energy unit (e.g., a battery) can be coupled to the lighting device to provide power, thereby creating a "self-powered" lighting device. Those skilled in the art will appreciate that a variety of other known power sources can be coupled to the percutaneous lighting device.

As previously explained, the elongate member 120 can also include one or more support members configured to stabilize the illumination device relative to tissue. As depicted in FIG. 1A, the support members 130, 140 are in the form of flanges that are disposed around the elongate member 120, and that are spaced a distance apart from one another for engaging tissue therebetween. One of the flanges, e.g., the proximal flange 140, is preferably rigid, while the other flange 130 can be configured as an expandable structure. For example, if the expandable structure is embodied as an inflatable flange 130, the flange 130 can be configured to be deflated, wholly or partially, when the illumination device 100 is being inserted through tissue. After the illumination device 100 is positioned through the tissue, the inflatable flange 130 can be expanded such that the structure can engage tissue, to limit movement of the illumination device 100. In another instance, one or both flanges 130, 140 can be removable to allow the flange 130, 140 to be placed onto the elongate member 120 after positioning the member 120 through desired tissue. For example, FIG. 2 illustrates another embodiment of a percutaneous illumination device 200 having a removable support member of flange 240. As shown, the elongate member 215 of the illumination device 200 is positioned through abdominal and stomach tissue 220 such that the illumination source 210 is disposed within a body cavity 280 while the opposite end 205 of the elongate member 215 remains outside of the body cavity, labeled as region 290. The removable flange 240 can then be fitted around the elongate member 215 to engage abdominal tissue 220 and secure the device 200. Though various depictions and descriptions of support members herein are embodied as flanges, many other types of structures can serve as support members, so long as they are compatible for engaging tissue and securing the illumination device in a desired orientation. Accordingly, non-limiting examples of support members can include clamps, annular rings with protruding spoked structures for engaging tissue, and other structures capable of engaging tissue and a portion of the illumination device to aid in orienting the device in a desired position.

In general, the use of support members, along with other portions of the illumination device (e.g., the elongate member), allow positioning of the illumination source in a desired direction to direct illumination. The support members 130, 140, 230, 240 can be spaced along the elongate member 120, 215, as shown in FIGS. 1A and 2, to sandwich tissue with enough compression to secure a direction of the illumination source 110, 210, while not being so compressive as to prevent the illumination source 110, 210 from being pointed in different directions. This can be achieved by spacing the support members 130, 140, 230, 240 apart by a distance a bit larger than the thickness of the tissue layer(s) to allow some small amount of angular displacement of the elongate member 120, 215. Alternatively, or in addition, an adjustable joint can be coupled to the illumination device to help enhance angular positioning of the illumination source. For the specific device depicted in FIG. 2, a ball-and-socket joint 260 is formed between the elongate member 215 and the support member 240 to provide an adjustable joint for directing the illumination source 210 in a desired angular direction. In particular, a ball is coupled on the proximal portion of the elongate member 215, and a socket is formed within the flange 240 for movably engaging the ball. The joint's friction can be configured to provide a desired trade-off between adjustability of the joint, and its ability to retain a particular angular configuration. Those skilled in the art will appreciate that many other types of adjustable joints can be utilized within the scope of the present application.

In use, percutaneous illumination devices, such as the exemplary ones depicted and described with regard to FIGS. 1A and 2, can be used to provide illumination to a body cavity. FIGS. 3A-3C provide various perspective views, at different magnifications, depicting the percutaneous illumination device 100 of FIG. 1A implanted to illuminate a stomach cavity 340. As depicted in FIGS. 3A-3C, the elongate structure 120 of the illumination device 100 pierces the gastric tissue 320 and the abdominal wall 330, with the end 105 remaining outside the body cavity. The opposite end, having the illuminating source 110, is within the stomach cavity 340. The support members 130, 140 can be spaced apart such as to sandwich one or more tissue layers therebetween. For example, as depicted in FIG. 3C, one support member 140 can be disposed on one side of the abdominal and gastric walls 320, 330 and the other support member 130 can be disposed on the opposite side of the abdominal and gastric walls 320, 330. The elongate member 120 can be positioned such that the illumination source 110 is directed in a desired direction, with the support members 130, 140 acting to substantially fix the elongate member 120 in the desired orientation. Upon fixing and activating the illumination source, the device can provide directed illumination anywhere within a body cavity independent of other devices, such as an endoscope or laparoscope. Though FIGS. 3A-3C depict the use of only one illumination device, any number of the devices can be positioned as desired throughout the body cavity and they can be directed to provide illumination to the areas sought to be viewed by a surgeon or other user. As well, while FIGS. 3A-3C show the use of the device for illuminating a stomach cavity, the percutaneous lighting device can also be used to illuminate other internal areas of a body (e.g., intestinal tract or portions of a chest cavity, etc.).

While various techniques can be used to insert the device through tissue, in one exemplary embodiment, the illumination device can be delivered endoscopically by a trans-oral route to a stomach cavity. For example, a sutured, or otherwise appropriately threaded, needle can be fed through a working channel of an endoscope. The free end of the suture can be coupled to the illumination device. The stomach can be inflated, using a gas, such that the gastric wall 320 is brought into proximity with the abdominal wall 330 as shown in FIG. 3B. The threaded needle can then be inserted into the gastric wall, through the abdominal wall and dermal tissue to the exterior of the body. The needle and threading can be subsequently pulled to pull the device through the endoscope and eventually through the tissue layers until one end of the elongate member is positioned on the external side of the dermal tissue. When a separate power source is utilized with the illuminating source, an electrical lead can be connected to the externally placed end of the elongate member to provide power. The trailing support member can engage the stomach wall to prevent the device from being pulled completely through the tissue layers. For example, for the embodiment shown in FIG. 1A, the support member 130 can be inflated to engage the gastric wall within the stomach cavity, and support member 140 can be placed on the exposed end of the elongate member after it is pulled through the tissue to engage the tissue surfaces between the support members 130, 140. For the embodiment shown in FIG. 2, support member 230 can engage the stomach wall, and the detachable flange 240 or other support member can be mated to the elongate member after it is pulled through the tissue to engage the tissues between the support members 230, 240. The elongate member can optionally be directed at a particular angle to provide a desired direction of illumination upon activating the illuminating source. This process can provide targeted illumination within a body cavity since penetrating from an inner cavity to the exterior allows for precise positioning of the illumination source. The steps of the process can be repeated multiple times for each illuminating device that is desired to be implanted.

The above exemplary embodiment is one example of how a percutaneous illuminating device can be utilized to provide illumination within a body. Those skilled in the art will appreciate that variations on these steps can be performed. For example, one alternative method of utilizing a percutaneous lighting device is to mount the device by penetrating tissue from an exterior body surface to within the body cavity or internal region to be illuminated. The stomach can be inflated, as described before, and a needle, threaded and coupled to the illumination device, can be inserted through the dermal tissue and into a body cavity. An endoscopic or laparoscopic instrument can be used to grasp the needle and pull the tethered illumination device into place such that the illumination source can properly illuminate a desired cavity location after fixation by one or more support members. Alternatively, where the elongate member includes a tissue-penetrating tip, such as tip 211 in FIG. 2, it can be directly penetrated through tissue either from a location within the body or from an external location, without the use of a needle and suture. In such a case, the elongate member preferably includes an expandable (e.g., inflatable) support member that can be expanded after the elongate member is penetrated through tissue to engage the tissue of the body cavity. Other variations include the use of different types of support members, utilizing the devices in other than endoscopic or laparoscopic procedures, and providing illumination in other body cavities and internal regions beyond the stomach. These variations and others are all contemplated within the scope of the present application.

Since one or more percutaneous illumination devices can be used to provide adequate illumination of a body cavity, another exemplary embodiment is directed to a kit for illuminating an internal region of a body of a patient. The kit includes a set of illuminating devices. As used herein, the term "set" refers to a group having one or more members. The illuminating devices can each be embodied as any of the devices described within the present application, with any number and combination of the features described for any particular embodiment. In one example, each of the illumination devices includes an elongate body that is adapted to be inserted into tissue, and at least one illumination source for illuminating a region around the device. The kit can also include a set of support devices, such as flanges, that are each adapted to be coupled to an illuminating device to provide stabilization at a desired angular orientation. The illumination devices can include additional features such as an adjustable joint as previously described, or the kit can include one of more additional sets of items such as a set of energy sources to be electrically coupled to the illumination sources. Kits consistent with the exemplary embodiment can provide an appropriate and convenient grouping of percutaneous illumination devices to be used in a particular surgical procedure.

Percutaneous illumination devices, including portions thereof, can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. By way of example, the percutaneous illumination devices shown in FIGS. 1 and 2 can be reconditioned after the device has been used in a medical procedure. The device can be disassembled, and any number of the particular pieces (e.g., the illumination source 110, the elongate body 120, any of the support members 130, 140, the electrical leads 150, 155, etc.) can be selectively replaced or removed in any combination. For instance, the illumination source can be replaced by a new illumination source, while the remaining pieces are sterilized for reuse. Replacement of pieces can also include replacement of portions of particular elements, such as the replacement of a ball on an elongate member as a part of a ball-and-socket joint. Upon cleaning and/or replacement of particular parts, the device can be reassembled for subsequent use either at a reconditioning facility, or by a surgical team immediately prior to a surgical procedure. Those skilled in the art will appreciate that reconditioning of a fastener-extracting device can utilize a variety of techniques for disassembly, cleaning/replacement, and reassembly. Use of such techniques, and the resulting reconditioned percutaneous illumination device, are all within the scope of the present application.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present invention. As well, one skilled in the art will appreciate further features and advantages of the invention based on the above-described embodiments. Accordingly, the invention is not to be limited by what has been particularly shown and described, except as indicated by the appended claims.

What is claimed is:

1. A percutaneous illumination device for illuminating a body cavity, comprising:
an elongate member having a proximal end, a penetrating tip disposed on the proximal end of the elongate member configured to penetrate through a tissue layer outwardly from inside the body cavity, a distal end configured to direct light from an illumination source to illuminate an area surrounding the elongate member and configured to extend through the tissue layer into a body cavity, a diameter in the range about 1 mm to about 5 mm, and a length in the range of about 25 mm to about 300 mm; and
first and second support members coupled to the elongate member and extending circumferentially therearound, the first support member being substantially rigid and having a first width, the first support member being disposed distal to the proximal end of the elongate member, the second support member being a non-jointed inflatable support member movable between an expanded configuration and a deflated configuration and having a second width in the expanded configuration that is less than the first width, the second support member being disposed distal to the first support member and proximal to the distal end, and the first and second widths being greater than a width of the elongate member and adapted to be positioned on opposite sides of a tissue surface to stabilize the elongate member.

2. The illumination device of claim 1, further comprising a light emitting diode disposed on the elongate member.

3. The illumination device of claim 1, wherein a terminal end of the elongate member includes a light source.

4. The illumination device of claim 1, wherein the first and second support members are spaced apart by a distance that is adapted to receive tissue therebetween.

5. The illumination device of claim 1, wherein at least one of the support members comprises a flange formed around the elongate member.

6. The illumination device of claim 1, wherein the elongate member includes an adjustable joint formed thereon and adapted to allow a distal portion of the elongate member to be positioned at an angle relative to a proximal portion of the elongate member.

7. The illumination device of claim 6, wherein the adjustable joint comprises a ball and socket joint.

8. The illumination device of claim 1, further comprising an energy source in electrical communication with the illumination source, the energy source coupled to the elongate member.

9. The illumination device of claim 1, wherein the elongate member includes an attachment structure for coupling a suture thereto.

10. The device of claim 1, wherein at least one of the first and second support members includes an adjustable joint formed therein configured to allow angular positioning of the illumination source.

11. A method of reconditioning the percutaneous illumination device of claim 1, comprising:
replacing or cleaning at least a portion of at least one of the elongate member, the illumination source, the first support member and the second support member.

12. A percutaneous illumination device for illuminating a body cavity, comprising:
an elongate member having a proximal portion, a penetrating tip disposed on the proximal portion of the elongate member configured to penetrate through a tissue layer outwardly from inside the body cavity, a distal portion with an illumination source configured to deliver light into a body cavity, a diameter in the range of about 1 mm to about 5 mm, and a length in the range of about 25 mm to about 300 mm; and first and second support members coupled to the elongate member, the first and second support members having a diameter greater than a diameter of the elongate member, the support members being configured to be positioned in contact with tissue to stabilize the elongate member in tissue, the first support member having an adjustable joint formed therein configured to allow the distal portion of the elongate member to be positioned at an angle relative to the proximal portion of the elongate member to allow angular positioning of the illumination source and the second support member being a non-jointed inflatable support member configured to be movable between an expanded configuration and a deflated configuration and positioned between the first support member and the illumination source.

13. The device of claim 12, wherein the joint comprises a ball and socket joint.

14. The device of claim 13, wherein the ball is disposed on the elongate member and the socket is formed within the first support member.

15. The device of claim 12, wherein the elongate member is substantially solid.

16. A method comprising:
inserting at least one illumination device according to claim 1 entirely into a body cavity;
puncturing an inside wall of the body cavity from inside the body cavity; and
inserting the at least one device into the punctured inside wall and through a tissue layer such that a distal portion of the at least one illumination device extends inside the body cavity and a proximal portion of the at least one illumination device extends outside the body cavity.

17. The method of claim 16, wherein the at least one illumination device is inserted into the body cavity transorally.

18. The method of claim 16, wherein the penetrating tip punctures the inside wall of the body cavity from inside the body cavity.

19. The method of claim 16, further comprising inserting a plurality of illumination devices entirely into the body cavity.

20. The method of claim 19, further comprising inserting the plurality of illumination devices into the punctured inside wall and through the tissue layer such that a distal portion of each illumination device extends inside the body cavity and a proximal portion of each illumination device extends outside the body cavity.

21. The method of claim 16, further comprising insufflating the body cavity with a gas to facilitate ease of insertion of the at least one illuminating device, wherein the body cavity is a stomach cavity.

* * * * *